United States Patent [19]
Nemet-Mavrodin

[11] Patent Number: 4,990,714
[45] Date of Patent: Feb. 5, 1991

[54] COMBUSTIVE MEMBRANE REACTOR AND PARAFFIN UPGRADING PROCESS

[75] Inventor: Margaret Nemet-Mavrodin, Cherry Hill, N.J.

[73] Assignee: Mobil Oil Corporation, Fairfax, Va.

[21] Appl. No.: 347,307

[22] Filed: May 4, 1989

[51] Int. Cl.$^5$ .................. C07C 7/144; C07C 2/76; C07C 2/00
[52] U.S. Cl. .................. 585/407; 585/415; 585/419; 585/818; 208/172
[58] Field of Search .............. 585/407, 415, 419, 818; 208/172

[56] References Cited

U.S. PATENT DOCUMENTS

| | | | |
|---|---|---|---|
| 2,769,693 | 11/1956 | Bearer | 208/172 |
| 3,136,713 | 6/1964 | Miale et al. | 208/113 |
| 3,254,023 | 5/1966 | Miale et al. | 208/120 |
| 3,267,023 | 8/1966 | Miale et al. | 208/111 |
| 3,760,024 | 9/1973 | Cattanach | 260/673 |
| 3,845,150 | 10/1974 | Yan et al. | 260/673.5 |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,536,196 | 8/1985 | Harris | 585/818 |

FOREIGN PATENT DOCUMENTS 2190397A 11/1987 United Kingdom .

Primary Examiner—Chung K. Pak
Attorney, Agent, or Firm—Alexander J. McKillop; Charles J. Speciale; Robert B. Furr, Jr.

[57] ABSTRACT

A process and reactor apparatus are disclosed for upgrading paraffinic feedstocks to olefinic and/or aromatic products. Hydrogen diffuses through a selectively permeable membrane from the reaction zone into a combustion zone where it reacts exothermically with an oxygen-containing fluid to supply at least a portion of the endothermic heat of reaction for the paraffin upgrading process. Additionally, in-situ separation of by-product hydrogen from the reactant mixture in the reaction zone increases yield of valuable olefinic and aromatic products.

13 Claims, 1 Drawing Sheet

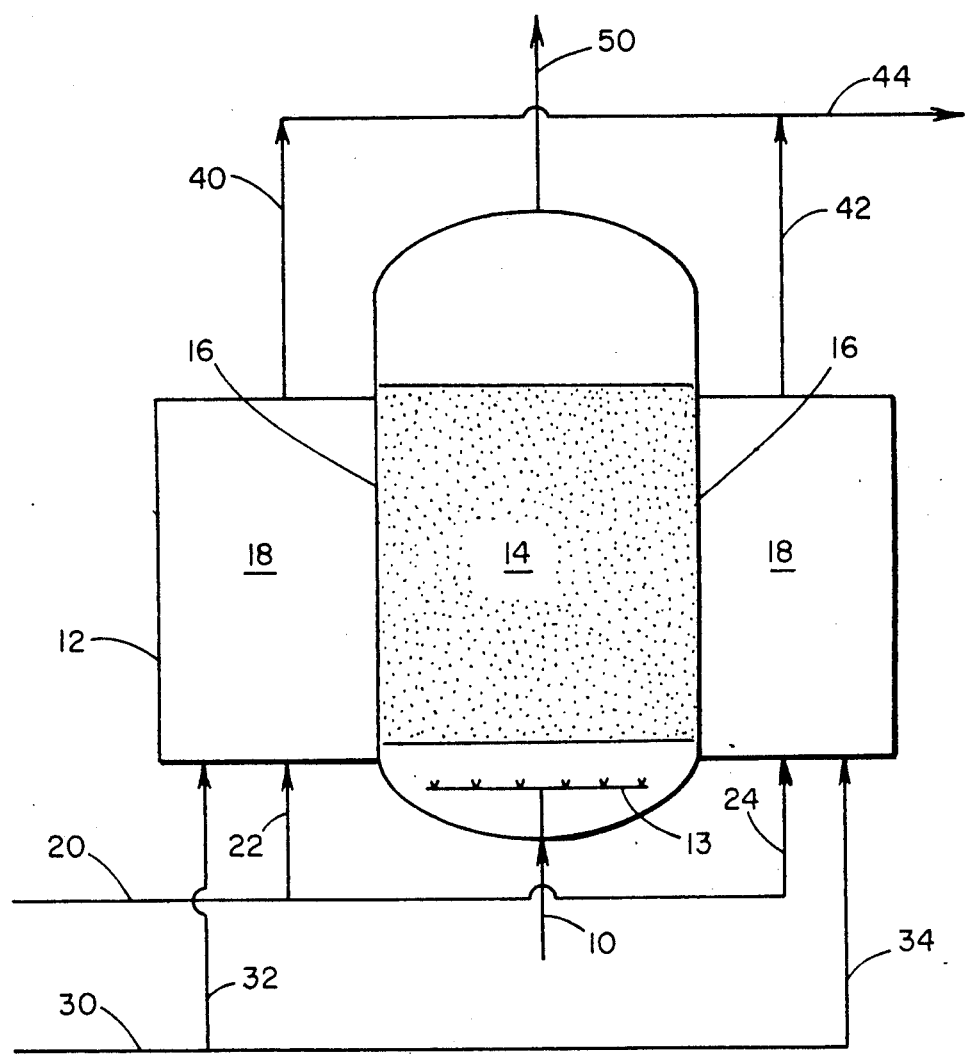

COMBUSTIVE MEMBRANE REACTOR AND PARAFFIN UPGRADING PROCESS

FIELD OF THE INVENTION

The present invention relates to the conversion of relatively low value light paraffinic streams to more valuable olefinic and aromatic streams. More in particular, the invention relates to a process for the dehydrogenation or aromatization of $C_2$–$C_6$ predominately paraffinic streams in which hydrogen by-product is withdrawn from the reaction zone through a selectively permeable membrane and at least a portion of the endothermic heat of reaction is supplied by the endothermic oxidation of the hydrogen by-product.

BACKGROUND OF THE INVENTION

Developments in zeolite catalysts and hydrocarbon conversion processes have created interest in utilizing light aliphatic feedstocks for producing $C_{5+}$ gasoline, diesel fuel, etc. In addition to basic chemical reactions promoted by medium-pore zeolite catalysts, a number of discoveries have contributed to the development of new industrial processes. These are safe, environmentally acceptable processes for utilizing aliphatic feedstocks. Conversions of $C_2$–$C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed to the understanding of catalytic olefin upgrading techniques and improved processes as in U.S. Pat. Nos. 4,150,062, 4,211,640 and 4,227,992. The above-identified disclosures are incorporated herein by reference.

Catalytic dehydrogenation and aromatization of light paraffinic streams, e.g. $C_2$–$C_4$ paraffins, commonly referred to as LPG, is strongly endothermic and typically carried out at temperatures between 540° and 820° C. (1000° and 1500° F.). While the incorporation of hydrogenation/dehydrogenation metals including gallium, platinum, indium, tin and mixtures thereof in zeolite catalysts may reduce the operating temperature to the range of about 400° to 600° C. (750° to 1100° F.), the problem of transferring sufficient heat to a catalytic reaction zone to carry out the paraffin upgrading reaction remains as an obstacle to commercialization of these processes.

Dehydrogenation of paraffins to olefins has recently generated increasing interest as the market value of olefinic intermediate feedstocks continues to rise. Light olefins, particularly $C_2$–$C_4$ olefins enjoy strong demand as building blocks for a wide range of valuable end products including fuels and specialized lubricants as well as thermoplastics.

Methods of supplying heat to an endothermic reaction zone also include indirect heat exchange as well as direct heat exchange. Indirect heat exchange is exemplified by a multi-bed reactor with inter-bed heating or a fluid bed reactor with heat exchange coils positioned within the catalyst bed. Direct heat exchange techniques include circulation of inert or catalytically active particles from a high temperature heat source to the reaction zone, or the coupling of a secondary exothermic reaction with the primary endothermic reaction in a single catalytic reaction zone. An example of such a secondary exothermic reaction is the oxidative dehydrogenation of a portion of the feedstream.

Known techniques for oxidative dehydrogenation are unfortunately less than 100% selective and at least a part of the valuable product is oxidized, adversely affecting not only selectivity and yield but also accelerating permanent steam deactivation of the zeolite catalyst by exposing the catalyst to the water of combustion at elevated reaction temperatures. Further, the incremental costs associated with maintaining a controlled supply of a suitable oxygen source, e.g. $NO_x$, $CO_2$ or $SO_3$, detracts from the commercial potential of such techniques.

Examples of such oxidative dehydrogenation processes include U.S. Pat. No. 3,136,713 to Miale et al teaches a method for heating a reaction zone by selectively burning a portion of a combustible feedstream in a reaction zone. Heat is directly transferred from the exothermic oxidation reaction to supply the endothermic heat for the desired conversion reaction.

Heat balanced reactions are also taught in U.S. Pat. No. 3,254,023 and 3,267,023 to Miale et al. Additionally, U.S. Pat. No. 3,845,150 to Yan and Zahner teaches a heat balanced process for the aromatization of hydrocarbon streams by combining the exothermic aromatization of light olefins with the endothermic aromatization of saturated hydrocarbons in the presence of a medium-pore zeolite catalyst.

Turning now to chemical reaction kinetics, it is well recognized that the extent of reaction may be increased by removing reaction products from contact with the reactants as the reaction products are formed. This principle finds application in U.S. Pat. No. 3,450,500 to Setzer et al. which teaches a process for reforming hydrocarbon feedstocks and withdrawing the hydrogen product from contact with the feedstock driving the equilibrium to favor increased hydrogen production.

Similarly, British Patent Application GB 2190397 A describes a process for producing aromatic hydrocarbons by catalytic paraffin dehydrocyclodimerization. The process upgrades $C_2$–$C_6$ paraffins, i.e. ethane, propane, butane or a mixture thereof to a mixture of aromatic hydrocarbons and hydrogen by-product in a reactor provided with a membrane capable of selective, in-situ transfer of at least a portion of the hydrogen in the mixture across the membrane. Catalysts useful in the paraffin upgrading process are said to include zeolites, and in particular gallium-containing zeolites.

It is believed that the paraffin dehydrogenation reaction is equilibrium limited when carried out in a conventional reactor due to relatively high hydrogen partial pressure Thus the state of the art of endothermic hydrogen-producing paraffin upgrading processes would clearly be advanced by a process and apparatus for increasing the extent of reaction while also providing a high temperature heat source to supply at least a portion of the endothermic heat of reaction.

SUMMARY OF THE INVENTION

The present invention provides a high temperature heat source for the endothermic paraffin aromatization process while at the same time increasing the extent of reaction by withdrawing hydrogen from the reaction zone through a selectively permeable membrane. Conversion in catalytic paraffin upgrading processes such as dehydrogenation and aromatization is believed to be equilibrium limited. Further, hydrogen is known to promote hydrocracking which is deleterious to product yield and selectivity.

By withdrawing hydrogen from the reaction zone as it is formed, the invention improves valuable product yield and selectivity. Moreover, the invention supplies much-needed thermal energy at suitably high temperatures to strongly endothermic paraffin aromatization or dehydrogenation reactions by combusting the hydrogen in indirect contact with the aromatization reaction zone.

The invention achieves these and other beneficial results in a process for upgrading a paraffinic feedstream comprising the steps of maintaining a reaction zone containing a zeolite catalyst in a reaction zone, the reaction zone being provided with a selectively permeable membrane capable of transferring at least a portion of the hydrogen by-product evolved in the reaction zone while substantially retaining hydrocarbon reactants and products within said reaction zone, charging the feedstream containing $C_2-C_6$ paraffins to the reaction zone under conversion conditions sufficient to convert at least a portion of said $C_2-C_6$ paraffins to aromatics and by-product hydrogen, transferring at least a portion of the by-product hydrogen through the selectively permeable membrane to a combustion zone by maintaining a hydrogen partial pressure differential between the reaction zone and the combustion zone such that the hydrogen partial pressure within the reaction zone exceeds the hydrogen partial pressure within the combustion one, charging an oxygen-containing fluid to said combustion zone at a rate sufficient to provide a stoichiometric excess of oxygen and to combust at least a portion of said by-product hydrogen, and indirectly transferring thermal energy from said combustion zone to said reaction zone.

Hydrogen generated as a by-product in the reaction zone diffuses through the selectively permeable membrane into the combustion zone driven by the differential hydrogen partial pressure between the two zones. The exothermic consumption of hydrogen in the combustion zone not only provides heat to the reaction zone for the paraffin upgrading process but also maintains a relatively uniform hydrogen partial pressure differential between the two zones.

DESCRIPTION OF THE DRAWING

The Figure is a simplified schematic diagram of the reactor unit of the present invention.

DETAILED DESCRIPTION

Hydrocarbon feedstocks which can be converted according to the present process include various refinery streams including coker gasoline, light FCC gasoline, $C_5-C_7$ fractions of straight run naphthas and pyrolysis gasoline, as well as raffinates from a hydrocarbon mixture which has had aromatics removed by a solvent extraction treatment. Examples of such solvent extraction treatments are described in *Kirk-Othmer Encyclopedia of Chemical Technology*, Third Edition, Vol. 9, 706–709 (1980). A particular hydrocarbon feedstock derived from such a solvent extraction treatment is a Udex raffinate. Propane- and butane-rich refinery streams commonly referred to as LPG are particularly preferred for upgrading to aromatics and olefins in the process of the present invention.

Catalysts useful in the process of the invention include metals or metal oxides on an inert support to promote paraffin dehydrogenation as well as zeolites, preferably medium-pore zeolites as described below for paraffin dehydrogenation and aromatization.

Zeolite catalysts having a high concentration of Bronsted acid reaction sites are understood to promote paraffin aromatization. Accordingly, an important criterion is selecting and maintaining zeolite catalyst inventory is to provide either fresh or regenerated catalyst having the desired properties. Typically, acid cracking activity (alpha value) can be maintained from high activity values greater than 40 to significantly lower values. If the process is carried out in a fluid bed of zeolite catalyst, alpha value may be maintained by controlling fresh catalyst makeup as well as catalyst deactivation and regeneration rates to provide an apparent average alpha value (based on total catalyst inventory) below 40, e.g. about 20.

Process Conversion Conditions

The details of the catalytic aromatization of paraffinic feedstocks are set forth in the references cited above which are incorporated by reference as if set forth at length herein. Catalytic aromatization of light $C_4$-aliphatic streams is further described in the article, "M2 Forming-A Process for Aromatization of Light Hydrocarbons", by N.Y. Chen and T.Y. Yan, Ind. and Eng. Chem. Process Des. Dev., 151 (1986), which article is incorporated herein by reference. Paraffin dehydrogenation proceeds readily under similar process conditions of temperature, pressure and space velocity. The preferred paraffin dehydrogenation catalyst, however, is a metal or metal oxide on an inert support.

TABLE 1

| Upgrading Reaction Process Conditions | |
|---|---|
| WHSV | Broad range: 0.3–300 hr$^{-1}$ |
| | Preferred range: 0.5–10 hr$^{-1}$ |
| Operating Pressure | Broad: 150–2170 kPa (7–300 psig) |
| | Preferred: 150–790 kpa (7–100 psig) |
| Operating Temperature | Broad: 400–820° C. (750–1500° F.) |
| | Preferred: 400–650° C. (750–1200° F.) |

Dehydration Catalysts

Paraffin dehydrogenation catalysts include oxides and sulfides of Groups IVA, VA, VIA, VIIA and VIIIA and mixtures thereof on an inert support such as alumina or silica-alumina. Thus, dehydrogenation may be promoted by sulfides and oxides of titanium, zirconium, vanadium, niobium, tantalum, chromium, xolybdenum, tungsten and mixtures thereof. Oxides of chromium alone or in conjunction with other catalytically active species have been shown to be particularly useful in dehydrogenation. Other catalytically active compounds include sulfides and oxides of manganese, iron, cobalt, rhodium, iridium, nickel, palladium, platinum and mixtures thereof.

The above-listed metals of Groups IVA, VA, VIA, VIIA and VIIIA may also be exchanged onto zeolites to provide a zeolite catalyst having dehydrogenation activity. Platinum has been found to be particularly useful for promoting dehydrogenation over zeolite catalysts.

Medium-Pore Zeolite Catalysts

The members of the class of zeolites useful in the process of the present invention have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecule of varying sizes to its internal structure is the Constraint Index of the zeolite. The method by which the Constraint Index is determined is described in U.S. Pat. No. 4,016,218, incorporated herein by reference for details of the method U.S. Pat. No. 4,696,732 discloses Constraint Index values for typical zeolite materials and is incorporated by reference as is set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600; the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention as aromatization catalysts and are disclosed in U.S. Pat. No. 4,350,835 and U.S. Pat. No. 4,686,312, both of which are incorporated by reference as if set forth in length herein.

Zinc-containing zeolite catalysts are also preferred for use in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Selectively Permeable Membrane

The present invention employs a selectively permeable membrane to retain paraffinic reactants as well as olefinic and aromatic products within a catalytic reaction zone while separating and withdrawing hydrogen from the reaction zone in-situ. Once diffused through the selectively permeable membrane, hydrogen is exothermically oxidized to water thus minimizing hydrogen partial pressure within the combustion zone.

A general survey of membrane technology is presented in *Kirk-Other Encyclopedia of Chemical Technology*, Third Edition, Vol. 15, 92–131 (1980). Suitable materials for the hydrogen-permeable membrane are discussed at length in British Patent Application GB 2190397, cited above, and include Pd, Ti, Zr, Ni, Co, Fe, Pt, V, Nb, Ta, and Ag, most preferably a palladium-silver alloy comprising 76% Pd and 24% Ag by weight. The British Patent Application teaches membrane thicknesses between 0.01 and 0.5 mm, preferably between 0.01 and 0.1 mm. At page 2, lines 1–14, the British Patent Application indicates that the membrane is sandwiched between rigid stainless steel plates having protrusions which support the membrane while allowing diffusion across the membrane.

The membrane of the present apparatus is preferably sandwiched between two perforate stainless steel plates. The perforations should be sufficiently small that the steel plate, rather than the selectively permeable membrane, retains the solid catalyst in the reaction zone. Thus the permeable membrane may alternatively be encased in a woven support such as a stainless steel screen having adequate strength to provide lateral support for the solid catalyst in the reaction zone.

U.S. Pat. No. 4,313,013 to Harris discloses a palladium or palladium alloy hydrogen diffusion membrane. Examples I and II at columns 3–5 show the separation of hydrogen from ethylene at a temperature of 450° C. (840° F.). and pressure of 167-170 kPa, falling within the broad and preferred process conditions of the present invention and suggesting that the membrane taught in the Harris reference would also be suitable for use in conjunction with the present invention.

Combustion Zone

In the preferred embodiment of the invention, the reactor is divided into a reaction zone and a combustion zone by a composite wall which includes a selectively permeable membrane. The combustion zone is preferably at least partially filled with inert solid particles to improve heat transfer between the combustion zone and the reaction zone. While relatively large particles such as alumina balls having a major diameter of up to about 2.5 cm are useful to improve heat transfer smaller, more easily fluidized particles are preferred. The inert solid particle are most preferably maintained in a state of sub-transport turbulent fluidization to maximize heat transfer between the combustion zone and the reaction zone.

Spent FCC catalyst is particularly preferred for use in the present invention due to its relatively low cost and low rate of attrition. Materials useful in the present invention must remain relatively inert and resist attrition at combustion temperatures and, to fluidize easily, must be characterized by a combination of size, shape and density as to be classified as Geldart Type A powders. For a discussion of fluidization in the Geldart Type classification system see U.S. Pat. No. 4,513,160 to Avidan, as well as Geldart 7 Powder Technology 285 (1973), both of which are incorporated by reference as if set forth at length herein. Briefly, Geldart Type A powders are easily fluidizable finely divided solids.

Reactor Unit Operation

Referring now to the figure, a paraffinic feedstream as described above enters the bottom of reactor vessel 12 through line 10. The feedstream is typically preheated to dehydrogenation or aromatization reaction temperature and is preferably maintained at a temperature just below that at which coke precursors in the feed thermally degrade to form coke. Examples of these coke precursors include oxygenates such as glycol and furfural.

Reactor vessel 12 preferably includes a fluid distributor 13 to evenly disperse the paraffinic feed as it flows upwardly into catalyst bed 14. Reaction zone 14 contains a catalyst tailored for the desired conversion reaction. For example, if the reactor unit is to be operated in a paraffin dehydrogenation mode, reaction zone 14 is filled with a dehydrogenation catalyst, i.e. a metal or metal oxide on an inert support. Alternatively, if aromatization of the paraffinic feed is desired, reaction zone 14 is filled with a composite catalyst comprising a zeolite, preferably a metal-containing medium-pore zeolite.

In the preferred embodiment, reactor vessel 12 is divided into a reaction zone 14 containing a solid catalyst and a combustion zone 18 by a hydrogen-permeable membrane 16 which selectively allows diffusion of hydrogen from reaction zone 14 into combustion zone 18. The membrane 16 is shown in the Figure as cylinder encasing a bed of catalyst within reaction zone 14. The membrane must have sufficient surface area to diffuse at least a part of the by-product hydrogen evolved in the reaction zone 14 to the combustion zone 18 given the available differential in hydrogen partial pressure between reaction zone 14 and combustion zone 18. Such design considerations are within the capability of one of ordinary skill in the art.

Combustion zone 18, shown annularly surrounding reaction zone 14, supplies at least a part of the endothermic heat of reaction required for the conversion reaction proceeding within reaction zone 14. In addition to the by-product hydrogen entering combustion zone 18 via the selectively permeable membrane 16, supplemental fuel may be added to combustion zone 18 through lines 22 and 24 which are fed by fuel header 20. The fuel is typically a light $C_3$-paraffinic fuel gas. An oxygen-containing combustion gas, typically air, flows to combustion zone 18 through lines 32 and 34, which are fed by conduit 30. One or more burner assemblies (not shown) may be positioned in combustion zone 18 to control mixing of combustion gas and supplemental fuel. Combustion zone 18 may optionally contain an inert solid to facilitate heat transfer between the hot combustion gases and the reaction zone.

Combustion products are withdrawn from combustion zone 18 through lines 40 and 42 which empty into a common combustion gas header 44. The hot combustion gases are then cooled to below about 190° C. (375° F.) in a heat recovery unit, e.g. a steam generation unit, treated as required to meet environmental quality standards and exhausted to atmosphere.

Changes and modifications in the specifically described embodiments can be carried out without departing from the scope of the invention which is intended to be limited only by the scope of the appended claims.

What is claimed is:

1. A process for upgrading a hydrocarbon feedstream containing $C_2$–$C_6$ paraffins comprising the steps of:
    (a) maintaining a reaction zone containing a zeolite catalyst, said reaction zone being provided with a selectively permeable membrane capable of transferring at least a portion of the hydrogen by-product evolved in said reaction zone while substantially retaining hydrocarbon reactants and products within said reaction zone;
    (b) charging said feedstream containing $C_2$–$C_6$ paraffins to said reaction zone under conversion conditions sufficient to convert at least a portion of said $C_2$–$C_6$ paraffins to aromatics and by-product hydrogen;
    (c) decreasing the hydrogen partial pressure within said reaction zone by transferring at least a portion of said by-product hydrogen through said selectively permeable membrane to a combustion zone, said combustion zone being separated from said reaction zone by said selectively permeable membrane to restrict mass transport between said reaction zone and said combustion zone to moieties not larger than hydrogen molecules, said hydrogen transfer being effected by maintaining a hydrogen partial pressure differential between said reaction zone and said combustion zone such that the hydrogen partial pressure within said reaction zone exceeds the hydrogen partial pressure within said combustion zone;
    (d) charging an oxygen-containing fluid to said combustion zone at a rate sufficient to provide a stoichometric excess of oxygen and to combust at least a portion of said by-product hydrogen to enhance diffusion of hydrogen across said selectively permeable membrane by continuously converting hydrogen diffused from said reaction zone to said combustion zone into combustion products comprising moieties larger than hydrogen molecules; and
    (e) indirectly transferring thermal energy from said combustion zone to said reaction zone.

2. The method of claim 1 wherein said catalyst comprises a zeolite having a Constraint Index of between about 1 and about 12.

3. The process of claim 2 wherein said zeolite has the structure of at least one selected from the group consisting of ZSM-5, ZSM-11, ZSM-12, ZSM-22, ZSM-23. ZSM-35 and ZSM-48.

4. The process of claim 2 wherein said zeolite contains at least one of the group consisting of Ga, Pt, In and Sn.

5. The process of claim 2 wherein said conversion conditions include pressures between 150 and 2170 kPa (7 and 300 psig), temperatures between 400 and 820° C. (750 and 1500° F.) and WHSV between 0.3 and 300 $hr^{-1}$.

6. The process of claim 2 wherein said conversion conditions include pressures between 150 and 790 kPa (7 and 100 psig), temperatures between 400 and 600° C. (750 and 1100° F.) and WHSV between 0.5 and 10 hr$^{-1}$.

7. The process of claim 2 further comprising maintaining said zeolite catalyst in a fixed bed.

8. The process of claim 2 wherein said catalytic reaction zone comprises a fluid bed of zeolite catalyst.

9. The process of claim 2 wherein said catalytic reaction zone comprises a fixed bed of zeolite catalyst.

10. The process of claim 2 further comprising maintaining inert solid particles within said combustion zone of step (c) to improve heat transfer between said combustion zone and said reaction zone.

11. The process of claim 10 further comprising fluidizing said inert solid particles within said combustion zone of step (c).

12. The process of claim 11 wherein said inert solid particles comprise a Geldart Type A powder.

13. The process of claim 11 wherein said inert solid particles comprise spent catalytic cracking catalyst.

* * * * *